(12) United States Patent
Schlangen et al.

(10) Patent No.: US 8,427,311 B2
(45) Date of Patent: Apr. 23, 2013

(54) LIGHTING DEVICE AND METHOD FOR PRODUCING SEQUENTIAL LIGHTING STIMULI

(75) Inventors: Lucas Josef Maria Schlangen, Eindhoven (NL); Lucius Theodorus Vinkenvleugel, Eindhoven (NL); Vanja Hommes, Eindhoven (NL)

(73) Assignee: Koninklijke Philips Electronics N.V., Eindhoven (NL)

( * ) Notice: Subject to any disclaimer, the term of this patent is extended or adjusted under 35 U.S.C. 154(b) by 338 days.

(21) Appl. No.: 12/812,057

(22) PCT Filed: Jan. 13, 2009

(86) PCT No.: PCT/IB2009/050115
§ 371 (c)(1),
(2), (4) Date: Jul. 8, 2010

(87) PCT Pub. No.: WO2009/090596
PCT Pub. Date: Jul. 23, 2009

(65) Prior Publication Data
US 2010/0277316 A1    Nov. 4, 2010

(30) Foreign Application Priority Data
Jan. 17, 2008 (EP) ..................................... 08150335

(51) Int. Cl.
*G08B 21/00* (2006.01)
(52) U.S. Cl.
USPC ..................... 340/540; 340/568.2; 340/555
(58) Field of Classification Search .................. 340/540, 340/541, 547, 545.3–545.6, 555, 565, 568.2, 340/575
See application file for complete search history.

(56) References Cited

U.S. PATENT DOCUMENTS

| | | | |
|---|---|---|---|
| 5,079,682 A | 1/1992 | Roberts | |
| 5,749,646 A | 5/1998 | Brittell | |
| 6,236,622 B1 | 5/2001 | Blackman | |
| 6,688,753 B2 | 2/2004 | Calon et al. | |
| 6,838,994 B2 | 1/2005 | Gutta et al. | |
| 7,280,439 B1 | 10/2007 | Shaddox | |
| 2003/0095476 A1* | 5/2003 | Mollicone et al. | 368/250 |
| 2005/0152128 A1 | 7/2005 | Campman | |
| 2006/0022214 A1* | 2/2006 | Morgan et al. | 257/99 |
| 2007/0086199 A1 | 4/2007 | Demarest et al. | |
| 2008/0103561 A1* | 5/2008 | Moscovici | 607/88 |
| 2010/0090612 A1* | 4/2010 | Spartano | 315/287 |

FOREIGN PATENT DOCUMENTS

| | | |
|---|---|---|
| AT | 413438 | 2/2006 |
| BE | 1015507 A3 | 5/2005 |
| DE | 20111906 U1 | 1/2002 |
| DE | 10056745 A1 | 5/2002 |

(Continued)

*Primary Examiner* — Daniel Previl

(57) ABSTRACT

The invention provides a lighting device (1) comprising one or more light sources (10) arranged to generate light, an accommodating device (5) having an external boundary (2) which is at least partly translucent and is arranged to accommodate the one or more light sources and a controller (40). The lighting device can generate two types of light. One or more lighting parameters selected from the group consisting of the first luminous intensity of the first type of light, the second luminous intensity of the second type of light, the color point of the first type of light and the color point of the second type of light can be controlled. This allows task lighting and atmosphere lighting. The invention is also directed to a method of providing a wake-up stimulus by means of such a lighting device.

15 Claims, 4 Drawing Sheets

FOREIGN PATENT DOCUMENTS

| | | |
|---|---|---|
| DE | 202005013164 U1 | 11/2005 |
| GB | 2422447 A | 7/2006 |
| JP | 6314595 A | 11/1994 |
| KR | 2006036068 A | 4/2006 |
| WO | 0136864 A2 | 5/2001 |
| WO | 0199475 A1 | 12/2001 |
| WO | 0211497 A1 | 2/2002 |
| WO | 2004049767 A1 | 6/2004 |
| WO | 2006038135 A1 | 4/2006 |
| WO | 2006074205 A1 | 7/2006 |
| WO | 2007069185 A1 | 6/2007 |
| WO | 2007071397 A1 | 6/2007 |
| WO | WO 2007/069185 * | 6/2007 |

* cited by examiner

LIGHTING DEVICE AND METHOD FOR PRODUCING SEQUENTIAL LIGHTING STIMULI

FIELD OF THE INVENTION

The present invention relates to a lighting device for generating a wake-up stimulus.

BACKGROUND OF THE INVENTION

Bright light exposure has proved to facilitate awakening. The light elevates the cortisol levels in healthy subjects. Dawn simulators are commercially available. These lighting devices increase the intensity of light prior to awakening to approximately 30 to 400 lux over a period of time ranging from 15 to 120 minutes. Then an audible alarm sounds. Dawn simulation improves the cortisol response and mood during awakening.

Document US 2003/0095476 describes an apparatus for a waking control system. The apparatus is intended to gradually introduce a stimulus, such as light, before a planned wake-up time, in order to wake the individual gradually so as to promote wellness. The document further describes the seasonal amount of light that is taken into account, as determined by the date. Document GB2422447 describes a dawn simulator alarm clock.

Document JP6314595 describes a lighting system. The lighting system turns on a lighting lamp and its illuminance is controlled to 2000 lux or more, while the related color temperature is controlled to 6000 Kelvin or more.

Lighting devices have the common characteristic feature that they use one lamp and that the transmitted light is white light.

Lighting devices comprising one or more light sources capable of generating different types of light of different colors are known in the art.

For instance, BE 1015507 describes a lighting assembly with two or more white lights, at least one of which is dimmable, and a separate color filter is provided on one side for each light, while there are no or no different color filters on the other side.

U.S. Pat. No. 6,688,753 describes a lighting device comprising a first lighting element, preferably a compact fluorescent discharge vessel and a second lighting element, preferably comprising a plurality of LEDs. During operation, the first lighting element has a comparatively high light output. In operation, the second lighting element has a light output which is relatively low in comparison with that of the first lighting element. The first or the second lighting element, or both, can be switched on. The lighting device allows remote-controlled switching between orientation light (night lamp) and normal light, using a toggle function in the lighting device.

OBJECT AND SUMMARY OF THE INVENTION

It is an object of the present invention to provide an improved lighting device for generating a wake-up stimulus.

According to a first aspect of the invention, the lighting device comprises:
a. one or more light sources arranged to generate light;
b. an accommodating device having an external boundary which is at least partly translucent and is arranged to accommodate the one or more light sources; and
c. a controller connected to the one or more light sources; wherein a first part of the external boundary and the one or more light sources are arranged to provide at least part of the light through the first part of the external boundary, thereby providing a first flux of a first type of light, the first type of light having a color and a first luminous intensity;

a second part of the external boundary and the one or more light sources are arranged to provide at least part of the light through the second part of the external boundary, thereby providing a second flux of a second type of light, the second type of light corresponding to white light and having a second luminous intensity; and the controller comprises a trigger input for receiving a trigger signal and is arranged to increase the first luminous intensity of the first type of light after receiving the trigger signal, wherein the color of the first type of light initially has a dominant wavelength in the range of 580 to 770 nm, and to subsequently increase the second luminous intensity of the second type of light.

Advantageously, an alternative lighting device for generating a wake-up stimulus is provided in this way. In nature, spectral variations occur during dawn and dusk with timescales ranging from a few minutes to half an hour. These lighting conditions influence a human's biological clock and wake-up behavior. It is therefore expected that the photoreceptive system that is subject to non-visual, biological effects of light develops an optimal sensitivity to variations of lighting parameters occurring within these timescales.

The sensitivity of the photoreceptive system caused by many non-visual, biological effects of light (like alertness, phase-shifting (jet-lag) and suppression of sleepiness) peaks in the short (blue) wavelength range (approximately 480 nm) of the spectrum. The intensity of the blue part of white light suppresses the production of melatonin in a human body. Melatonin is a hormone closely related to the body's biological clock or circadian rhythm. Normally, melatonin levels in humans rise in the evening, remain high most of the night while being asleep, and then drop in the morning upon awakening. The sensitivity of this photoreceptive system to blue light has been found to increase when the blue light exposure is preceded by exposure with red light (approximately 620 nm).

The lighting device according to the invention implements these features so as to improve the effectiveness of the wake-up light by spectral tuning and timing of light. The lighting device starts generating red light so as to improve the sensitivity of the photoreceptive system and then increases the intensity of white light so as to stimulate the photoreceptive system in suppressing the production of melatonin. At the end of the sleep cycle, a human will be in stage 1, 2, or in the REM (Rapid Eye Movement) sleep phase. During this phase, a human can be waked up by the presence of light. The eyelids can be considered as a red color pass filter. By applying red light only, this light will reach the photoreceptive system through the eyelids, which will enhance the sensitivity to blue light. When a human wakes up due to the presence of light, he will experience this as relaxing. By opening his eyelids, the blue part of the white light can reach the photoreceptive system. As the photoreceptive system is more sensitive to the blue light because the red-like light has previously been applied, the amount of melatonin in the human decreases more rapidly, which reduces the wake-up time.

The color of the light having a dominant wavelength in the red part of the frequency spectrum can be moved towards white light on the black body radiator color temperature line, while the intensity of the light increases. In this way, the contribution (in %) of photons in the red wavelength range changes towards a contribution (in %) for daylight at noon. In this way, the lamp provides the blue light that is necessary to activate the photoreceptive system and suppress the production of melatonin.

In an embodiment, the controller is arranged to increase the second luminous intensity of the second type of light after the first luminous intensity exceeds a predetermined light intensity. This embodiment allows use of a lighting device which generates two fixed types of light, i.e. the red-like light and the white light. The red-like light is used to improve the sensitivity of the photoreceptive system, and the white light provides the necessary blue light. In an embodiment, the controller is arranged to switch off the flux of the first type of light when the second luminous intensity exceeds a predetermined light intensity.

In an embodiment, the controller is arranged to increase the first luminous intensity to a value in the range of 1 to 50 lux in a period of time ranging from 5 to 45 minutes, and to increase the second luminous intensity to a value in the range of 50 to 800 lux at the position of the user's eyes in a subsequent period of time ranging from 5 to 30 minutes. These features allow the spectral range and timing of the generated light of the wake-up stimulus to be tuned to each individual so as to obtain the optimum wake-up effect in the morning.

In an embodiment, the lighting device is arranged to generate the first type of light and the second type of light in substantially different directions relative to the lighting device. These features allow a change of the spectral intensity as well as the angular distribution of the light during a dawn simulation. For example, the red-like light is emitted directly or indirectly to the face of a human via a wall or ceiling, while the white light illuminates the whole room.

The white and red light can be generated simultaneously. Moreover, the light emission and the angular distributions of the white and colored light sources may have different directions. Direct whitish light may be used for the wake-up stimulus but also for functional/task lighting. A luminaire designed as an object has a more attractive form factor as compared to more traditional luminaries. For example, a traditional whitish bedside luminaire can be replaced by the proposed white and red light emitting object. White light allows pleasant in-bed reading, whereas the separately tunable light allows generating the red-like light for the wake-up stimulus but also creates a special bedroom atmosphere.

In an embodiment, the color point of the first type of light moves from the initial red light to the black body locus. The color point of the second type of light, which is especially substantially white light, is on the black body locus (Planckian or Planckian locus) or close to the black body locus, particularly within 10 SDCM (standard deviation of color matching), and more particularly within 5 SDCM from the black body locus. The terms "SDCM" and black body locus or Planckian are well known in the art.

In an embodiment, the lighting device is arranged to generate the first type of light and the second type of light in substantially different directions relative to the lighting device. For instance, the second type of light may only illuminate part of the external boundary (through which at least part of the light is transmitted) of the lighting device, thereby providing a white light emitting object, whereas the first type of light is especially produced as a beam of light, for instance, for directly illuminating the eyes of a human, or a wall or a ceiling (exterior of the lighting device), for indirectly illuminating the human with the red light and for generating a special room atmosphere. The beam of light provides the necessary red light during generation of the wake-up stimulus so as to improve the sensitivity of the photoreceptive system. In such a case, the second type of light is distributed in a flux circumferentially surrounding at least part of the lighting device, whereas the first type of light is a beam with an aperture angle of, for instance, 60°.

The lighting device may accommodate one or more light sources. In a particularly advantageous embodiment, the one or more light sources comprise a first light source (which may include a plurality of first light sources) and a second light source (which may include a plurality of second light sources), wherein the first light source and the first part of the external boundary are arranged to generate the first type of light, and wherein the second light source and the second part of the external boundary are arranged to generate the second type of light. In this way, one type of light source is arranged to generate the first type of light, and another type of light source is arranged to generate the second type of light. This functional distinction may allow relatively easy control of the device and thus provides a lighting device for generating a more effective wake-up stimulus and a lighting device for controlling the room atmosphere. Note that the term "light source" may also include a plurality of light sources (see also below).

The phrases "a first part of the external boundary and the one or more light sources are arranged to provide at least part of the light through the first part of the external boundary, thereby providing a first flux of a first type of light" and "wherein the first light source and the first part of the external boundary are arranged to generate the first type of light" and similar phrases herein take those embodiments into account in which the color of the first type of light is substantially determined by the color of the light generated by the one or more light sources, as well as those embodiments in which the color of the first type of light is substantially determined by the combination of the color of the light generated by the first light source or sources in combination with the optical properties of the first part of the external boundary. For instance, the latter may be colored, thereby influencing the color of the first type of light. Likewise, this applies to similar phrases with respect to the second type of light and the second part of the external boundary. As will be evident to the person skilled in the art, optional color filters may further influence the color of the first and/or second type of light.

The term "external boundary" herein refers to the external wall of the housing. It indicates the exterior of the device and refers to the outer part or parts of the device which may be seen by an observer when a substantially intact device is in use.

The controller may have a number of functions (see below), including at least those of controlling one or more lighting parameters such as luminous intensity and/or the color point of one or both types of light, for instance, as a function of one or more input signals retrieved from a device selected from the group consisting of a user input device, a clock, a sensor, and memory settings from a memory of the controller. Furthermore, the lighting object comes with an optional, remote-controlled user interface (user input device) that allows independent control of the one or more lighting parameters defined herein. Hence, the controller may communicate with the one or more light sources (during use).

In a specific embodiment, the controller is arranged to control one or more lighting parameters selected from the group consisting of the first luminous intensity of the first type of light, the second luminous intensity of the second type of light, the color point of the first type of light and the color point of the second type of light. In addition to the minimum lighting parameters to be controlled by the controller, as defined in claim 1, the controller may thus control more parameters. This has the advantage that the device can be used for more diverse lighting features, for instance, dedicated to specific tasks (wake-up stimulus, other functional light), times of day, mood (i.e. state of mind), etc. In this way, both types of light can be controlled with respect to color and intensity. In a specific embodiment, the controller is arranged to control at least the color point of the first type of light and one or more lighting parameters selected from the group consisting of the first luminous intensity of the first type of light, the second luminous intensity of the second type of light and the color point of the second type of light. In a more specific embodiment, the controller is arranged to control at least the color point of the first type of light so as to move from red-like light to the black body locus, the first luminous intensity of the first type of light, the second luminous intensity of the second type of light and the color point of the second type of light.

As mentioned above, the lighting device may perform the task of generating a wake-up stimulus and task lighting and, optionally, the user (or other parameters) may influence the lighting parameters as described herein. In a specific embodiment, the lighting device according to the invention further comprises a sensor, (during use) in communication with the controller, arranged to sense one or more sensor parameters selected from the group consisting of outside temperature, outside light intensity, daylight color temperature, and weather conditions, and the controller is arranged to control the flux of the first type of light and the flux of the second type of light in dependence upon the one or more sensorial parameters. In another embodiment, the lighting device comprises a sound sensor for sensing and detecting an audible alarm signal and generating the trigger signal. The term "sensor" may include one or more sensors, i.e. one or a plurality of sensors. The sensor may be integrated within the lighting device or it may be separate, i.e. arranged separately from the lighting device. This may advantageously provide an intelligent device which automatically adapts the one or more lighting parameters as described herein, depending upon its sensor signals.

In a particularly advantageous embodiment, one or more of the one or more lighting parameters selected from the group consisting of luminous intensity and color point of the first type of light are dependent upon one or more lighting parameters selected from the group consisting of luminous intensity and color temperature of the second type of light. This advantageously provides, for instance, effects at which a high intensity of white light (second type of light) for performing, for instance, one or more tasks is accompanied by cool colors of the first type of light. This appears to be preferred by users. Likewise, when the white light is reduced in intensity, i.e. when the luminous intensity is reduced, this may be accompanied by relatively warm colors of the first type of light. For instance, when reducing the intensity during the evening when reading a book, warm colors as atmosphere light seem to be generally appreciated. The terms "control" and "controlling" are known in the art. Controlling the luminous intensity herein particularly refers to embodiments in which the luminous intensity may have a plurality of different values, particularly at least three different values, such as 100%, 70% and 30% of its maximum, more particularly at least ten different values. In one embodiment, the luminous intensity may be varied stepwise. In another embodiment, it may be varied substantially continuously. Controlling the color point herein particularly refers to embodiments in which the color point may have a plurality of different values, particularly at least two different values, more particularly at least ten different values. In one embodiment, the color point may be varied stepwise. In another embodiment, it may be varied substantially continuously.

In a specific embodiment, one light source, or one type of light source may be applied. In this specific embodiment, the lighting device further comprises a variable optical filter arranged to filter part of the light of the one or more light sources, thereby generating the first type of light having a variable color and the second type of light being white light. Such color filters, or, for instance, color filter wheels, are known in the art. Advantageously, one type of light source and its optionally concomitant peripheral equipment needs to be used.

According to a further aspect of the invention, a method of providing a wake-up stimulus by means of a lighting device as defined in any one of the claims comprises the steps of generating a first flux of a first type of light with an increasing first luminous intensity after receiving a trigger signal, the first type of light initially having a color with a dominant wavelength in the range of 580 to 770 nm, and subsequently generating a second flux of a second type of light with an increasing second luminous intensity, having a color corresponding to white light. This method provides an improved dawn atmosphere in a room in that it first provides a red-like color which gradually changes into white light.

BRIEF DESCRIPTION OF THE DRAWINGS

Embodiments of the invention will now be described, by way of example only, with reference to the accompanying schematic drawings in which corresponding reference symbols indicate corresponding parts.

DESCRIPTION OF EMBODIMENTS

Figure 1:
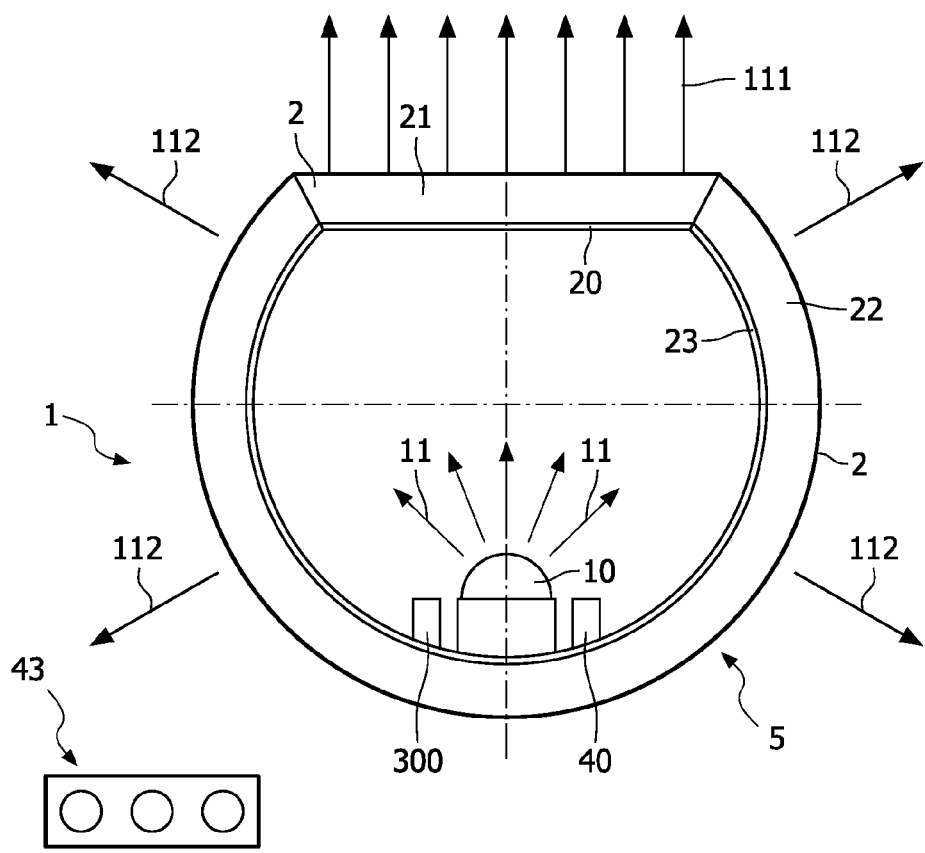
FIG. 1 schematically shows an embodiment of the lighting device according to the invention.
Figure 2A:
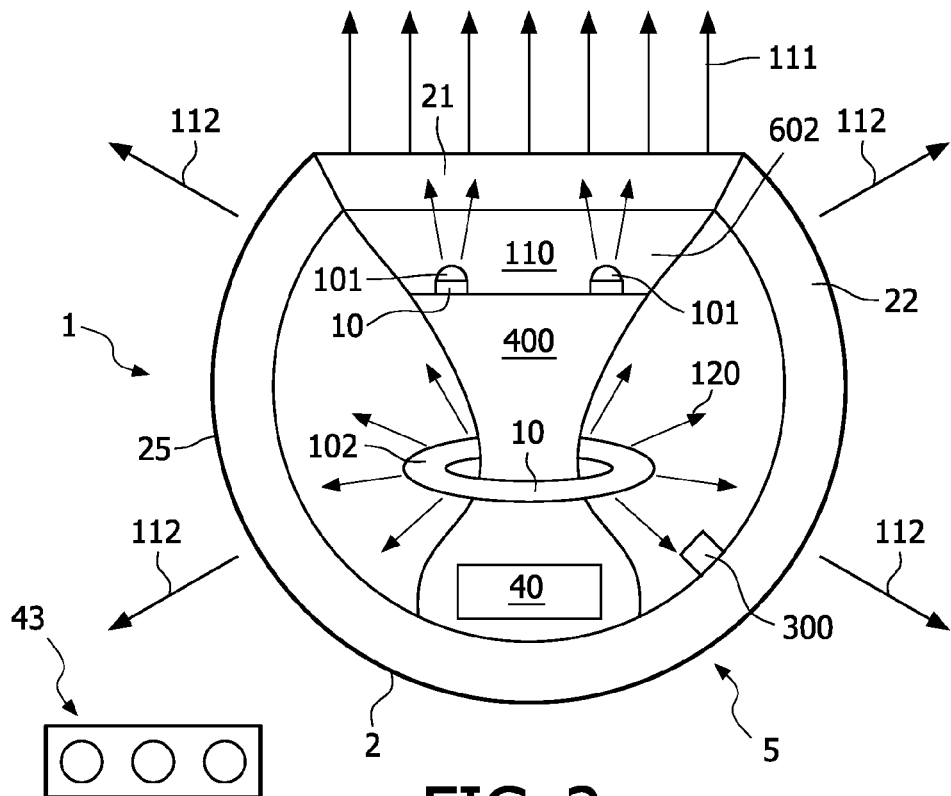
FIGS. 2a and 2b schematically show alternative lighting devices according to embodiments of the invention.
Figure 2B:
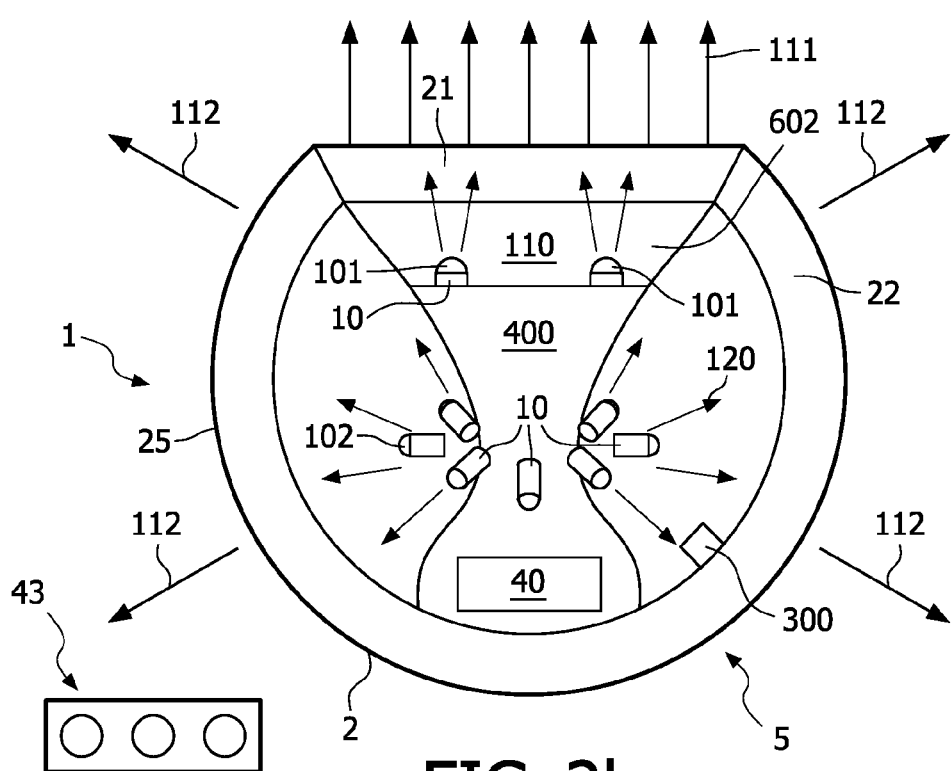

FIGS. 1, 2a and 2b show embodiments of the invention. These Figures schematically show a lighting device 1 comprising one or more light sources 10 which are arranged to generate light. Light is denoted by reference numeral 11. The lighting device 1 comprises an accommodating device, or housing, 5 having an external boundary, or wall, 2 which is at least partly translucent and is arranged to accommodate the one or more light sources 10. The boundary or wall 2 of the device 1 may be an integral piece or may consist of one or more pieces (assembled to an accommodating device 5). The accommodating device 5 is arranged to circumferentially surround the one or more light sources 10. The accommodating device 5 may have any shape. In one embodiment, the boundary 2 is arranged in such a way that, other than through boundary 2, substantially no light 11 or no light 11 at all of the one or more light sources escapes from the lighting device 1. Hence, the accommodating device 5 and boundary 2 circumferentially surround the one or more light sources 10.

The lighting device 1, more specifically the boundary or wall 2 of the accommodating device 5 comprises a first part 21, which allows part of the light of the one or more light sources 10 to escape to the exterior of the accommodating device 5, i.e. the first part 21 of the external boundary 2, and the one or more light sources 10 are arranged to provide at least part of the light 11 through the first part 21 of the external boundary 2, thereby providing a first flux of a first type of light 111. This first type of light 111 has a variable color and a first luminous intensity (which may also be variable).

Furthermore, the lighting device 1, more specifically the boundary or wall 2 of the accommodating device 5 comprises a second part 22, which allows part of the light of the one or more light sources 10 to escape to the exterior of the accommodating device 5, i.e. the second part 22 of the external boundary 2, and the one or more light sources 10 are arranged to provide at least part of the light 11 through the second part 22 of the external boundary 2, thereby providing a second flux of a second type of light 112. This second type of light 112 is white light and has a second luminous intensity (which may also be variable).

The at least one or more light sources 10 may comprise one or more lamps selected from the group consisting of filament lamps, fluorescent lamps (especially tubular luminescent (TL) lamps and compact fluorescent lamps (CFL)), halogen lamps, low-pressure gas discharge lamps, high-pressure gas discharge lamps, LEDs, and optionally also OLEDs. In an embodiment, lamp 10 comprises one or more lamps selected from the group consisting of low-pressure gas discharge lamps (CFL, TL) and LEDs. The term "LEDs" (light-emitting diodes) is herein understood not to include OLEDs (organic light-emitting diodes). The light sources 10 herein described may be lamps known to the person skilled in the art. In one embodiment, the one or more light sources 10 comprise LEDs or a combination of LEDs and halogen lamps.

The term "light" herein particularly refers to visible radiation (VIS), i.e. radiation in the range of about 380 to 780 nm. For instance, a set of blue, green and red LEDs may be used as light source 10. When such multiple sources of respective multiple colors (of the generated light) are used as light source or sources 10, they may be arranged in such a way that they can generate white light (by color mixing). Likewise, this may be achieved by mixing blue light of a blue light-emitting source and yellow light of a yellow light-emitting source (including white LEDs based on blue LEDs and a yellow light-emitting phosphor), as known in the art.

The first and the second part 21, 22 of the external boundary 2 comprise a translucent material. The translucent material may be a roughened transparent material. Methods of making translucent materials are known in the art. Examples of suitable transparent materials which can be used to accommodate the light sources 10 may be selected, for instance, from the group consisting of glass, polymethyl acrylate (PMA), polymethyl methacrylate (PMMA) (Plexiglas or Perspex), cellulose acetate butyrate (CAB), polycarbonate, polyvinyl chloride (PVC), polyethylene terephthalate (PET), and glycol modified polyethylene terephthalate (PETG), which materials may be provided as transparent sheets. In another embodiment, the sheet material comprises an acrylate, for instance, PMA or especially PMMA. Such materials are also known in the art as transparent plastics. In yet another embodiment, the sheet comprises transparent plastics commercially known as PERSPEX™ or PRISMEX™. Other substantially transparent materials known to the person skilled in the art may also be used. Combinations of two (or more) materials may be used.

Within its external boundary 2, the device 1 may further comprise diffusers, mirrors, optical filters, fiber optics, reflectors, etc., which are not shown. The device may use an external or an internal power supply, such as (pen light) batteries, which are not shown.

The lighting device 1 further comprises a controller 40 connected to the light sources 10. This controller 40 may be arranged within or outside the accommodating device 5 and may comprise a plurality of controller parts arranged within and outside the accommodating device 5. The controller 40 is arranged to control one or more lighting parameters selected from the group consisting of the first luminous intensity of the first type of light 111, the second luminous intensity of the second type of light 112, the color point of the first type of light 111 and the color point of the second type of light 112. The controller 40 may control one or more of these lighting parameters, preferably at least two, for instance, as a function of a sensor signal or from a user (see below). The controller 40 may be arranged to communicate with one or more other lighting devices 1. Communication can be realized via a wired or a wireless connection.

Figure 3:
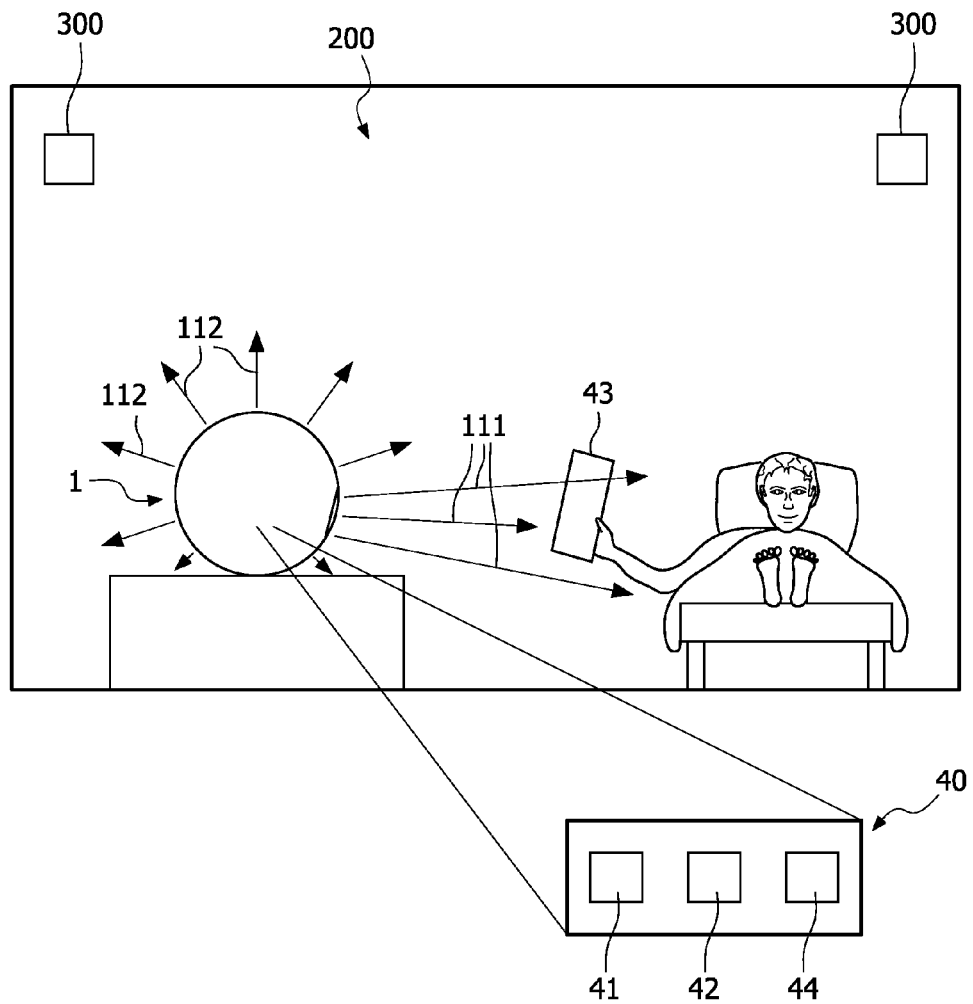
FIG. 3 schematically shows a lighting device in a bedroom.

The proposed lighting device 1 allows a combination of two functions: task lighting by means of (direct) whitish light 112 and atmosphere illumination by means of (particularly indirect) colored light 111. For instance, FIG. 3 schematically shows a device 1 in use. The lighting device 1 is arranged as a bedside luminaire in a bedroom 200. Furthermore, a person lying in bed in this bedroom 200 is indicated. By way of example, the person has a user input device 43, such as a remote control. There may also be one or more sensors 300 in bedroom 200, although instead thereof or in addition thereto, the accommodating device may also accommodate one or more sensors 300.

In this way, a lighting device 1 is advantageously provided, an embodiment of which particularly allows illumination (the first type of light 111) of, for instance, walls in room 200, thereby providing a mood, ambiance, or atmosphere light function, whereas the second type of light 112 may provide functional illumination, thereby allowing tasks to be carried out, such as reading, etc. The former function is non-functional lighting, herein briefly indicated as atmosphere function or atmosphere lighting. Since colored light is usually not appreciated for visual tasks, an embodiment of the device of the invention provides the atmosphere light function, on the one hand, and, on the other hand, the lumination or lighting function that can be used for visual tasks such as reading, working, etc. The terms "luminance" and "lumination" are known in the art and refer to a measure of the brightness of a surface. The terms "illuminance" and "illumination" are also known in the art and refer to the amount of light incident on a surface.

Figure 4:
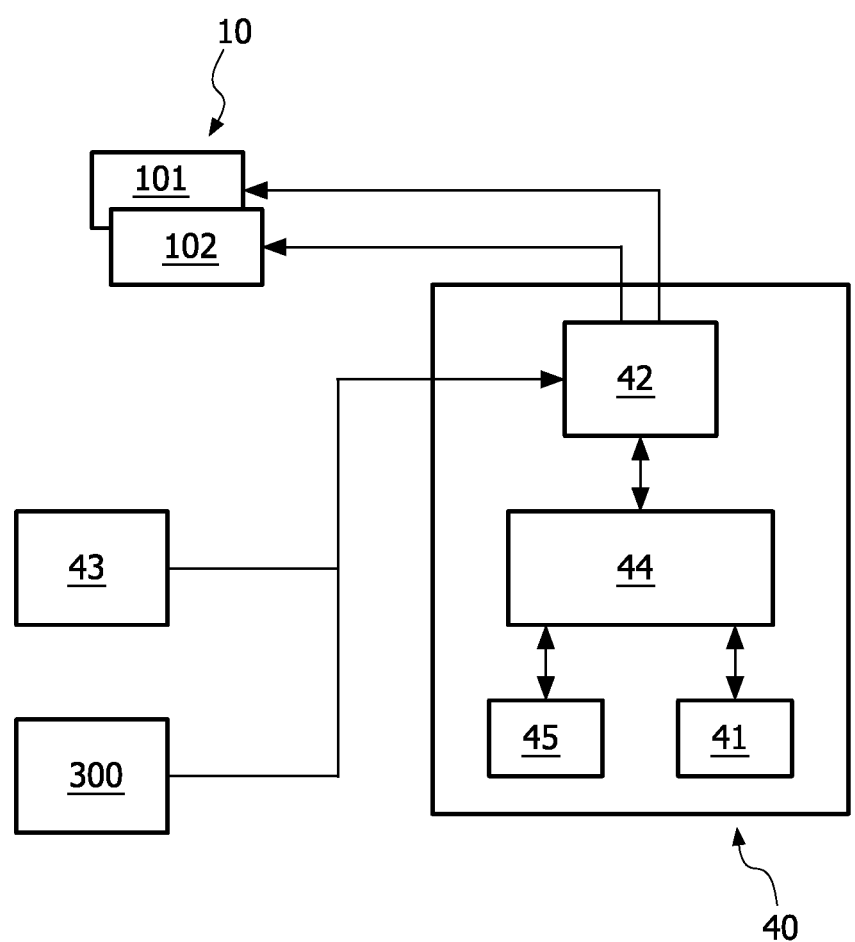
FIG. 4 schematically shows a general embodiment of a lighting device according to the invention.

As mentioned above and as further shown in FIG. 4, the lighting device 1 further comprises a controller (or control means) 40 connected to the one or more light sources 10 (an embodiment of which consists of one or more light sources 101 and one or more light sources 102, respectively, see below, cf. FIGS. 2a and 2b). In a specific embodiment, the controller 40 may comprise a processor 44 designed to process one or more input signals into one or more output signals, e.g. based on executable instructions which may be stored in a memory 41 connected to the processor 44. Furthermore, the processor 44 may be connected to an input-output unit 42, configured to (i) receive one or more input signals from one or more devices selected from the group consisting of (1) one or more sensors 300, (2) a remote clock device (not shown), (3) another lighting device 1 and (4) a user input device 43 and to (ii) send one or more output signals so as to control the intensity and/or color of the two types of light 111,112. The processor 44 may also be connected to a clock 45 (shown inside controller 40, but an external clock is also possible), which allows the processor 44 to drive device 1 in a time-dependent manner.

According to the invention, the controller 40 comprises a trigger input for receiving a trigger signal. In a preferred embodiment, the trigger signal is generated by a clock device built into or being in communication with the lighting device. The user can program the clock by entering a wake-up time. The trigger input will be generated during a period of time before the wake-up time. The period of time may be user-programmable and may range from 0 to 90 minutes. The controller 40 is arranged to increase the first luminous intensity of the first type of light 111 after receiving the trigger signal. The color of the first type of light 111 initially has a dominant wavelength in the range of 600 to 750 nm. After a predefined period of time, the second luminous intensity of the second type of light is gradually increased from a very low intensity, i.e. in the range of 0 to 5 lux, to an intensity in the range of 50 to 800 lux. The increase of intensity of the first and the second type of light 111, 112 may be linear, exponential, or in accordance with any other predefined course. The controller 40 may be further arranged to generate an audible alarm at the moment the second type of light 112 is generated or has reached a predetermined intensity.

The user input device 43 may be arranged to be in physical contact with the accommodating device 5 or it may be integrated within accommodating device 5; however, as is schematically shown in FIG. 3, the user input device may also be an external user input device 43, i.e. a remote control.

The user input device 43 may comprise, for instance, switches such as touch controls, slide switches, etc. for controlling one or more of the lighting parameters described hereinbefore, such as the intensity of the light source or sources 10, or for selecting the desired color of the different types of light 111,112, respectively, depending upon the application of lighting device 1, the user's mood, etc. The lighting device 1 can be used as, for instance, a wake-up lamp, a bedside lamp, a bed-head light, a relax lamp, an atmospheric light, a dawn/dusk simulation lamp, etc.

In an embodiment, the user input device 43 comprises a touch control. The touch control generates a signal indicating a user's touch. The controller 40 is arranged to increase or decrease the second luminous intensity by a predetermined amount after each touch. In this way, a user can change the intensity of the white light in a stepwise manner. In one embodiment, the intensity cyclically passes through the following intensities: off, first intensity, second intensity, and third intensity, wherein the first intensity is smaller than the second intensity which is smaller than the third intensity. The third intensity corresponds to the maximum intensity. In a further embodiment, the touch control signal indicates the time length of a touch. In this case, a short touch is interpreted as switching the second type of light on or off, and a longer touch, i.e. longer than half a second, is interpreted as a command to increase or decrease the intensity of the second type of light, with the length of time determining the extent of the increase or decrease. This embodiment allows a user to perform a dimming action.

The controller 40 may have pre-defined settings, or user-selectable settings, or both. Possibly intelligent biophysical input parameters may be used to automatically translate someone's behavior (motion, voice, music selection, facial expression as monitored by a camera) or activities (waking up, reading, falling asleep) into a certain setting of the lighting object. These parameters may be sensed by one or more sensors 300. Hence, the lighting device 1 may perform the task of atmosphere lighting and task lighting and, optionally, the user (or other parameters) may influence the lighting parameters as described hereinbefore. In a specific embodiment, the lighting device 1 therefore also comprises one or more sensors 300 arranged to sense one or more sensorial parameters selected from the group consisting of a person's presence in bed, his mood, facial expression, activities, and his behavior in room 200.

Furthermore, the intensity and/or color of the first and the second type of light 111 and 112, respectively, may be dependent upon external parameters such as time, temperature, light intensity of external sources (such as the sun), which may be measured by one or more sensors, denoted by reference numeral 300. The controller 40 may control the intensity of one or more of the light sources 10 via known means for controlling such light sources 10, such as ballasts (not shown).

In a specific embodiment, the second type of light 112 illuminates, in use, the room 200, thereby enabling the person to perform one or more desired tasks, whereas in another embodiment, the first type of light 111 particularly directed to the eyes of a human provides a beam of light so as to improve the wake-up stimulus.

The lighting device 1 of the invention can be applied in any environment where people sleep and general lighting and atmosphere light may be needed, such as in bedrooms, hospitals, clinics, hotels, etc.

Some specific embodiments, schematically shown in FIGS. 1, 2a and 2b will now be described.

FIG. 1 schematically shows an embodiment further comprising a (variable) optical filter 20 arranged to filter part of the light 11 of the one or more light sources 10, thereby generating the first type of light 111 having a (variable) color and the second type of light 112 being white light. The filter 20 only filters part of the light 11. In this way, part of the light may be colored, thereby providing colored light 111 (first type of light), whereas the second type of light 112 is substantially white. In this embodiment, the one or more light sources 10 substantially provide white light. Such sources 10 may be white emitting LEDs, triband lamps or other lamp types that provide light, either by themselves or in combination. In one embodiment, the optical filter 20 can be made variable by using a color filter wheel. The color filter wheel comprises a multitude of color filters in which the spectrum of the light gradually moves from red-like light to a color on the black body locus. The temperature of a black body as it is heated through its range of colors can be graphically represented as a line extending through the CIE 1931 Chromaticity Diagram. This line is known as the black body locus. A black body is a theoretical object which absorbs all light incident on it and emits light of different wavelengths, dependent on the temperature to which it is heated.

In another embodiment, the optical filter 20 is a foil wound on two reels. The filtering characteristic of the foil longitudinally moves from red-like light to a color on the black body locus. By winding the foil from one reel to the other, the lighting device 1 will generate a first type of light 111 whose color spectrum gradually moves from red-like light to a color on the black body locus.

A controllable device 23 which allows blocking of the light 11 of the light sources 10 may be present in a position between the one or more light sources 10 and the second part 22 of the external boundary 2. In this way, the lighting device 1 will provide only the first type of light 111, whereas no second type of light 112 will be provided by the second part 22 of the external boundary 2. The controllable device 23 may be an LCD layer which has a transparent state and a non-transparent state. The LCD allows control of the transparency providing a dimming function.

This embodiment allows the use of only one type of light source. A wake-up stimulus will begin by exposure of the red-like light 111 via the first part. If the one or more light sources 10 generate only white light, an optical filter 22 is present to filter the white light so as to obtain the first type of light 111, and when the intensity and/or lighting period exceed a predetermined value, the controllable device 23 will be opened and thus provide the second type of light 112.

If the one or more light sources 10 can generate light 11 with any visible radiation in the range of about 380 to 780 nm, no optical filter 20 is necessary for generating the wake-up stimulus. In this case, the one or more light sources 10 start generating the red-like light which will be transmitted via the first part 21 of the external boundary 2 so as to generate a flux of a first type of light. The controller will gradually change the relatively high contribution (in %) of red photons in the first type of light towards a total photon density for daylight at noon. When the total photon density exceeds a predetermined value, the controllable device 23 will be gradually moved from a non-transparent to a transparent state.

However, the embodiments schematically shown in FIGS. 2a and 2b are more preferred. Here, there are two types of light sources 10, i.e. a first source 101 for providing the first type of light 111 and a second source 102 for providing the second type of light 112. The first source(s) is (are) indicated as LEDs. Note that no color filter 20 is shown. However, one or more of such color filters may optionally be present. The one or more light sources 10 comprise first light sources 101 and second light sources 102. In this embodiment, the first sources 101 are arranged in a cavity 110 which is formed by first part 21 and a body 400. Cavity 110 may have the form and properties of a reflector 602. However, the accommodating device 5 may also accommodate one or more separate reflectors 602 so as to house the one or more light sources 10, more particularly the one or more first light sources 101 and to particularly collimate light from these respective light sources. Body 400 may consist of or comprise a cooling element. Body 400 may further comprise controller 40 or, in one embodiment, such a controller 40 may be attached to body 400, although this controller is not necessarily integrated with this body 400 or with accommodating device 5. Lighting device 1 further comprises the second type of sources 102, which may be one or more fluorescent (white emitting) lamps in this embodiment.

In this embodiment, the accommodating device 5 is constructed to have at least two substantially separated cavities. A first cavity 110 is arranged and constructed to accommodate the first light source or sources 101 and to allow at least part of the light of the first light sources to pass through at least part of the first part 21 of the boundary 2, thereby generating, during use, the first type of light 111. A second cavity 120 is arranged and constructed to accommodate the second light source or sources 102 and to allow at least part of the light of the second light sources to pass through at least part of the second part 22 of the boundary 2, thereby generating, during use, the second type of light 112. In one embodiment, the first and second cavities 110,120 are constructed to prevent substantial mixing of the light of the first light sources and the second light sources 101,102, respectively, within boundary 2 of accommodating device 5.

The only difference between the embodiment schematically shown in FIG. 2b and that schematically shown in FIG. 2a is that a halogen lamp or lamps instead of fluorescent lamps is applied as the second light source or sources 102.

More particularly, the first light sources 101 are LEDs for providing colored light, such as triband LEDs, or a plurality of LEDs whose light may be used to set up a gamut for the desired colors. Particularly also second light sources 102 may be, for instance, LEDs, although also one or more fluorescent (white emitting) lamps selected from the group of filament lamps, fluorescent lamps (especially tubular luminescent (TL) lamps and compact fluorescent lamps (CFL)), halogen lamps, low-pressure gas discharge lamps, high-pressure gas discharge lamps, LEDs, and optionally also OLEDs may be used.

As indicated in FIGS. 1, 2a and 2b, the first type of sources 101 illuminates, during use, the first part 21 of the boundary 2, and the second type of sources 102 illuminates the second part 22 of the boundary 2 of the accommodating device. The boundary 2 has an external surface 25 with a total surface area. In one embodiment, the external surface area of the first part 21 of the external boundary 2 covers between about 2% and 50%, preferably between about 5% and 33% of the total surface area of the external boundary 2. In another embodiment, the external surface area of the second part 22 of the external boundary 2 covers between 30% and 98%, preferably between about 44% and 95% of the total surface area of the external boundary 2. These examples, schematically shown in FIGS. 1, 2a and 2b, have an external boundary 2 which essentially consists of only the first part 21 and the second part 22. However, in other embodiments, a part of the external boundary 2 may also be non-transparent.

The external boundary 2 may further have parts that are non-transparent or non-translucent. The total surface area of surface 25 of the external boundary 2 is substantially the sum of the external surface area of the first part 21, the external surface area of the second part 22 and other optional parts, which may be non-transparent or non-translucent. In one embodiment, the lighting device 1 is constructed in such a way that no more light from the one or more light sources 10 escapes from the accommodating device 5 than escapes from the lighting device 1 through the first and the second part of the external boundary 2. Hence, in such an embodiment, the accommodating device 5 can be described as a substantially closed housing.

Some specific embodiments for a wake-up stimulus generation algorithm executed by the controller 40 will be described in more detail below.

A first embodiment of a wake—up stimulus generation algorithm comprises the following subsequent actions:

1. At t=0: switching the first type of light 111 on at a very low intensity, i.e. 0.001 to 0.1 lux;
2. t=0 to t=y min, wherein y is in the range of 5 to 45 minutes: increasing the light intensity of the first type of light 111 gradually to 1 to 50 lux; optionally, the frequency spectrum of the first type of light 111 gradually moves towards the black body locus;
3. At t=y min: switching the second type of light 112 on at a low intensity; preferably with an intensity corresponding to the intensity of the first type of light 111;
4. t=y min to t=y+z min, wherein z is in the range of 5 to 45 minutes, increasing the second type of light 112 to an intensity in the range of 50 to 800 lux, optionally increasing the color temperature of the white light by adding other spectral components;
5. t=y+z min: providing an audible stimulus, e.g. an alarm sound, audio, or video.

The first embodiment of a wake-up stimulus generation algorithm is very suitable for a very relaxed wake-up experience. A predetermined period of time (y+z minutes) before the desired wake-up time, the device 1 will first provide red-like light which gradually moves to the white light with a high intensity. The red-like light will pass the eyelids so as to increase the sensitivity of the photoreceptive system. In the period preceding the wake-up moment, a human does not sleep very deeply and may be awakened by the light. When this happens, the light will not have its highest intensity, which is comfortable for the human to open his eyes. At that moment, the blue part of the white light can reach the photoreceptive system, which will be more effective as the red-like light has increased the sensitivity of the photoreceptive system. The user can wake up slowly and leave his bed after he has heard the audible signal.

In a second embodiment, which is substantially similar to the first embodiment, at t=0 simultaneously with switching on the first type of light 111, an audible stimulus is given so as to wake up a human from a deep sleep. After this, the human will have a light sleep. This algorithm enables the user to wake up early and have a relaxed wake-up period. After his reaction to the audible stimulus, he might stay in bed. As he will not normally have a deep sleep immediately, the intensity of the first or the second type of light 111,112 may be sufficient to give the user a more natural wake-up experience. The audible stimulus may be generated by a built-in clock device or an external clock device. In the latter case, the lighting device may comprise a sound sensor (300) for sensing and detecting an audible alarm signal and generating the trigger signal, which indicates t=0.

A third embodiment of a wake-up stimulus generation algorithm comprises the following subsequent actions:
1. At t=0: switching the first type of light 111 on at a very low intensity, i.e. 0.001 to 0.1 lux;
2. t=0 to t=y min, wherein y is in the range of 5 to 45 minutes: increasing the light intensity of the first type of light 111 gradually to 1 to 50 lux; optionally, the frequency spectrum of the first type of light 111 gradually moves towards the black body locus;
3. t=y min: providing an audible stimulus, e.g. an alarm sound, audio, or video.
4. At t=y min: switching the second type of light 112 on at a low intensity; preferably with an intensity corresponding to the intensity of the first type of light 111;
5. t=y min to t=y+z min, wherein z is in the range of 5 to 45 minutes, increasing the second type of light 112 to an intensity in the range of 50 to 800 lux, optionally increasing the color temperature of the white light by adding other spectral components.

The third embodiment provides a time-efficient wake-up stimulus. Prior to the third action, the photoreceptive system is already made more sensitive to the blue part of the white light. Very soon after the audible wake-up stimulus, sufficient white light will be generated to reduce the melatonin in a human, enabling him to reduce the wake-up period. The third embodiment is very suitable for persons who sleep at irregular times, or have a short period of sleep, for example, truck drivers, bus drivers, or pilots. The third embodiment provides a wake-up device which improves the activation effect and reduces the necessary wake-up period. Furthermore, the lighting device may be used as a night lamp, or a reading lamp during traveling.

In the embodiment described above, the intensity gradually increases. The increase may be linear, stepwise, exponential or in accordance with any other suitable curve to increase the light from a low to a high intensity.

In the event that a sensor 300 detects whether the eyes of a human are open, said signal may be used as a trigger signal to start the generation of the white light.

A sensor on the window or outside the house may be present to steer the spectral and dynamic settings of the wake-up signal. Sensed parameters may be the outside temperature, light intensity and/or color temperature of the daylight, weather condition, and the course of the color during dawn/dusk/twilight/sunrise/sunset.

In the embodiments described above, the instant time determines the moment when the second type of light is switched on. Instead of time, the intensity of the first type of light 111 may be used to switch on the second type of light. In this case, the lighting device 1 comprises a sensor which measures the intensity of the first type of light. In one embodiment, the sensor is attached in the lighting device so as to directly measure the intensity of the one or more light sources 101. The algorithm is adapted to switch on the second type of light when the intensity of the first type of light exceeds a predetermined value. The predetermined intensity may be in the range of 1 to 50 lux.

As mentioned above, the lighting device 1 (or object) may simultaneously emit white light 112 and colored light 111, i.e. a lighting device 1 in which part 22 of the outer wall 2 basically emits white light 112 (for task illumination) and the other part 21 of the outer wall 2 emits red-like light 111 (particularly indirectly or directly), on a human's face nearby. Possible variations include:
a) fixed setting of both white light 112 and colored light 111;
b) adjustable intensity (and/or color temperature) of white light 112; fixed colored light 111;
c) adjustable brightness and color (hue and saturation) of colored light 111; fixed white light 112;
d) adjustable intensity (and/or color temperature) of white light 112; adjustable brightness and color (hue and saturation) of colored light 112;
e) the device 1 can be designed to stand on the floor, a bedside table or a table (as depicted in FIG. 3), or it can be suspended. In a preferred embodiment of the invention, a user's head is directly or indirectly illuminated by colored light via the ceiling or wall, whereas the task light shining in all directions is basically white.

The user interface or user input device 43 ("local" or "remote") controls the lighting generated by the light-emitting object as selected by the user. The interface or input device 43 may comprise control action buttons shown in an intuitive way in which the end user can navigate through the available settings. An intelligent microprocessor may allow a user to generate a dynamic effect via an algorithm. More than one lighting device 1 can be operated via a single-user interface device or user input device 43.

Intelligent (bio)physical input parameters and/or audio/video monitoring can be used to automatically translate someone's behavior (motion, voice, music selection, facial expression) or activities (waking up, reading, falling asleep) into a certain setting of the lighting object or its dynamics. There are various non-limiting possibilities, which are summarized below:

To detect the users mood/emotion, one or more sensors 300 can be applied as a separate device or devices and/or combined within the user interface 43. Alternatively, video/audio recordings can be used to detect voice and/or facial expression (smiling, sad, laughing, open/closed eyes, waking up, drowsy, sleepy);

A connection to an (alarm) clock 45 is used to assist a waking-up/falling asleep process with a (dynamic) lighting effect. Auditory signals generated by the (alarm) clock 45 can also be used as a trigger to (gradually) switch on the lighting device 1;

The lighting device 1 is equipped with a sound detector that classifies the choice of music played at home. The device 1 adjusts the settings of the lighting device 1 to the genre of music being played.

Part of the lighting device (or lighting object) emits white light 112, while part of the lighting object emits colored light 111, simultaneously, when desired. The intensity and color of the colored light can be set. Moreover, the intensity and color temperature of the white light can be set independently of the colored light setting.

Hence, in one embodiment, the invention provides a lighting device 1 comprising one or more light sources 10 arranged to generate light 111,112, an accommodating device 5 having an external boundary 2 which is at least partly translucent and is arranged to accommodate the one or more light sources 10, and a controller 40. The lighting device 1 can generate two types of light 111,112. One or more lighting parameters selected from the group consisting of the first luminous intensity of the first type of light 111, the second luminous intensity of the second type of light 112, the color point of the first type of light 111 and the color point of the second type of light 112 can be controlled. This allows the device 1 to generate the wake-up stimulus according to the invention, and provides task lighting and atmosphere lighting.

It should be noted that the above-mentioned embodiments illustrate rather than limit the invention, and that those skilled in the art will be able to design many alternative embodiments without departing from the scope of the appended claims. In the claims, any reference signs placed between parentheses shall not be construed as limiting the claim. Use of the verb "comprise" and its conjugations does not exclude the presence of elements or steps other than those stated in a claim. The article "a", "an" or "the" preceding an element does not exclude the presence of a plurality of such elements. The invention may be implemented by means of hardware comprising several distinct elements, and by means of a suitably programmed computer. In the device claim enumerating several means, several of these means may be embodied by one and the same item of hardware. The mere fact that certain measures are recited in mutually different dependent claims does not indicate that a combination of these measures cannot be used to advantage.

The invention claimed is:

1. A lighting device comprising:
   a) at least one light source arranged to generate light;
   b) an accommodating device having an at least partly translucent external boundary arranged to accommodate the at least one light source; and
   c) a controller for controlling light output from the accommodating device, where
      1. a first part of the external boundary and the at least one light source are adapted to provide, through the first part of the external boundary, a first flux of a first type of light having a color and a first luminous intensity;
      2. a second part of the external boundary and the at least one light source are adapted to provide, through the second part of the external boundary, a second flux of a second type of light corresponding to white light and having a second luminous intensity;
      3. the controller: (i) when triggered, effects said provision of the first type of light, such that the color initially has a dominant wavelength in the range of 580 to 770 nm and the first luminous intensity progressively increases, and (ii) subsequent to said triggering, progressively increases the second luminous intensity of the second type of light.

2. The lighting device according to claim 1 where the controller controls the color of the first type of light to move towards the black body radiator color temperature line.

3. The lighting device according to claim 1 where the controller increases the second luminous intensity of the second type of light after the first type of light has been switched on.

4. The lighting device according to claim 1 where the controller effects switching off of the flux of the first type of light after the second type of light has been switched on.

5. The lighting device according to claim 1, where the controller increases the first luminous intensity to a value in the range of 1 to 50 lux in a period of time ranging from 5 to 45 minutes, and increases the second luminous intensity to a value in the range of 50 to 800 lux in a subsequent period of time ranging from 5 to 30 minutes.

6. The lighting device according to claim 1 where the lighting device effects generation of the first type of light and the second type of light in substantially different directions relative to the lighting device.

7. The lighting device according to claim 1 where the at least one light source comprise a first light source and a second light source, where the first light source and the first part of the external boundary are arranged to generate the first type of light, and where the second light source and the second part of the external boundary are arranged to generate the second type of light.

8. The lighting device according to claim 1 where the first light source comprises at least one LED and the second light source comprises at least one lamp selected from a group consisting of filament lamps, fluorescent lamps, halogen lamps, low-pressure gas discharge lamps, high-pressure gas discharge lamps, LEDs, and OLEDs.

9. The lighting device according to claim 1 where the controller is adapted to control at least one of a plurality of lighting parameters as a function of at least one input signal retrieved from a device selected from a group consisting of a user input device, a clock device, a sensor and memory settings from a memory of the controller.

10. The lighting device according to claim 1 where the lighting device comprises a sensor for communicating with the controller and arranged to sense one or more sensorial parameters selected from a group consisting of outside temperature, outside light intensity, the color temperature of the daylight, and weather conditions, and where the controller is adapted to control the flux of the first type of light and the flux of the second type of light in dependence upon the one or more sensorial parameters.

11. The lighting device according to claim 1 where the lighting device comprises an optical filter arranged to filter part of the light of the at least one light source, thereby generating the first type of light.

12. The lighting device according to claim 1 where the lighting device comprises a user input device for generating a user input signal and where the controller is adapted to vary the second luminous intensity under the control of the user input signal.

13. The lighting device according to claim 1 where the lighting device comprises a sound sensor for sensing and detecting an audible alarm signal and generating a trigger signal for triggering the controller.

14. A method of providing a wake-up stimulus by means of a lighting device according to claim 1, where the method comprises the steps of generating a first flux of a first type of light with an increasing first luminous intensity after receiving a trigger signal, the first type of light initially having a color with a dominant wavelength in the range of 580 to 770 nm, and subsequently generating a second flux of a second type of light with an increasing second luminous intensity and having a color corresponding to white light.

15. A lighting device comprising:
    a) at least one light source arranged to generate light; and
    b) a controller connected to the at least one light source;

where the at least one light source is arranged to provide a first flux of a first type of light having a color and a first luminous intensity and to provide a second flux of a second type of light corresponding to white light and having a second luminous intensity; and where the controller: (i) when triggered, effects said provision of the first type of light such that the color initially has a dominant wavelength in the range of 580 to 770 nm and the first luminous intensity progressively increases, and (ii) subsequent to said triggering, progressively increases the second luminous intensity of the second type of light.

* * * * *